United States Patent [19]
Rice et al.

[11] Patent Number: 5,743,849
[45] Date of Patent: Apr. 28, 1998

[54] DISPOSABLE PROTECTIVE SLEEVE FOR A LARYNGOSCOPE AND METHOD OF USING THE SAME

[75] Inventors: Mark J. Rice, Johnson City, Tenn.; William T. Kearney, III, Lexington, Ky.; William T. Williams, Jonesborough, Tenn.; Ganesh V. Phatak, Lexington, Ky.; Timothy P. Maupin, Fairfield, Ohio

[73] Assignee: Blue Ridge Products, LP, Gray, Tenn.

[21] Appl. No.: 694,776

[22] Filed: Aug. 9, 1996

[51] Int. Cl.⁶ .................................................. A61B 1/32
[52] U.S. Cl. ...................................... 600/186; 600/198
[58] Field of Search ........................... 600/186, 203, 600/125, 121, 122, 124, 185, 198

[56] References Cited

U.S. PATENT DOCUMENTS

| | | |
|---|---|---|
| D. 316,898 | 5/1991 | Park . |
| 2,797,684 | 7/1957 | Moore .......................... 600/203 X |
| 3,426,749 | 2/1969 | Jephcott . |
| 4,565,187 | 1/1986 | Soloway . |
| 4,579,108 | 4/1986 | Bauman . |
| 4,583,527 | 4/1986 | Musicant et al. . |
| 4,757,381 | 7/1988 | Cooper ............................ 600/121 |
| 4,834,077 | 5/1989 | Sun . |
| 4,878,486 | 11/1989 | Slater . |
| 4,884,558 | 12/1989 | Gorski et al. . |
| 4,972,825 | 11/1990 | Vescovo, Jr. . |
| 4,979,499 | 12/1990 | Sun . |
| 5,063,907 | 11/1991 | Musicant et al. . |
| 5,065,738 | 11/1991 | Van Dam . |
| 5,168,863 | 12/1992 | Kurtzer ............................ 600/124 |
| 5,347,995 | 9/1994 | Slater et al. . |
| 5,359,991 | 11/1994 | Takahashi ....................... 600/122 |
| 5,363,843 | 11/1994 | Daneshvar ...................... 600/122 |
| 5,406,939 | 4/1995 | Bala ................................ 600/121 |
| 5,438,976 | 8/1995 | Nash . |
| 5,460,165 | 10/1995 | Mayes ............................ 600/186 |

*Primary Examiner*—Richard J. Apley
*Assistant Examiner*—Denise Pothier
*Attorney, Agent, or Firm*—Foley & Lardner

[57] ABSTRACT

A disposable protective sleeve used for covering laryngoscopes has a sheath and a shield integrally formed of a flexible material. The sheath defines a hollow cavity adapted to enclose a laryngoscope blade. The shield is attached to the sheath and is suited to cover a portion of the laryngoscope handle. The disposable sleeve is molded of a flexible plastic in a size and shape to conform to a particular size and shape of laryngoscope blade. After use, the sleeve is disposed of and the laryngoscope is covered with a new sleeve before being used again.

14 Claims, 16 Drawing Sheets

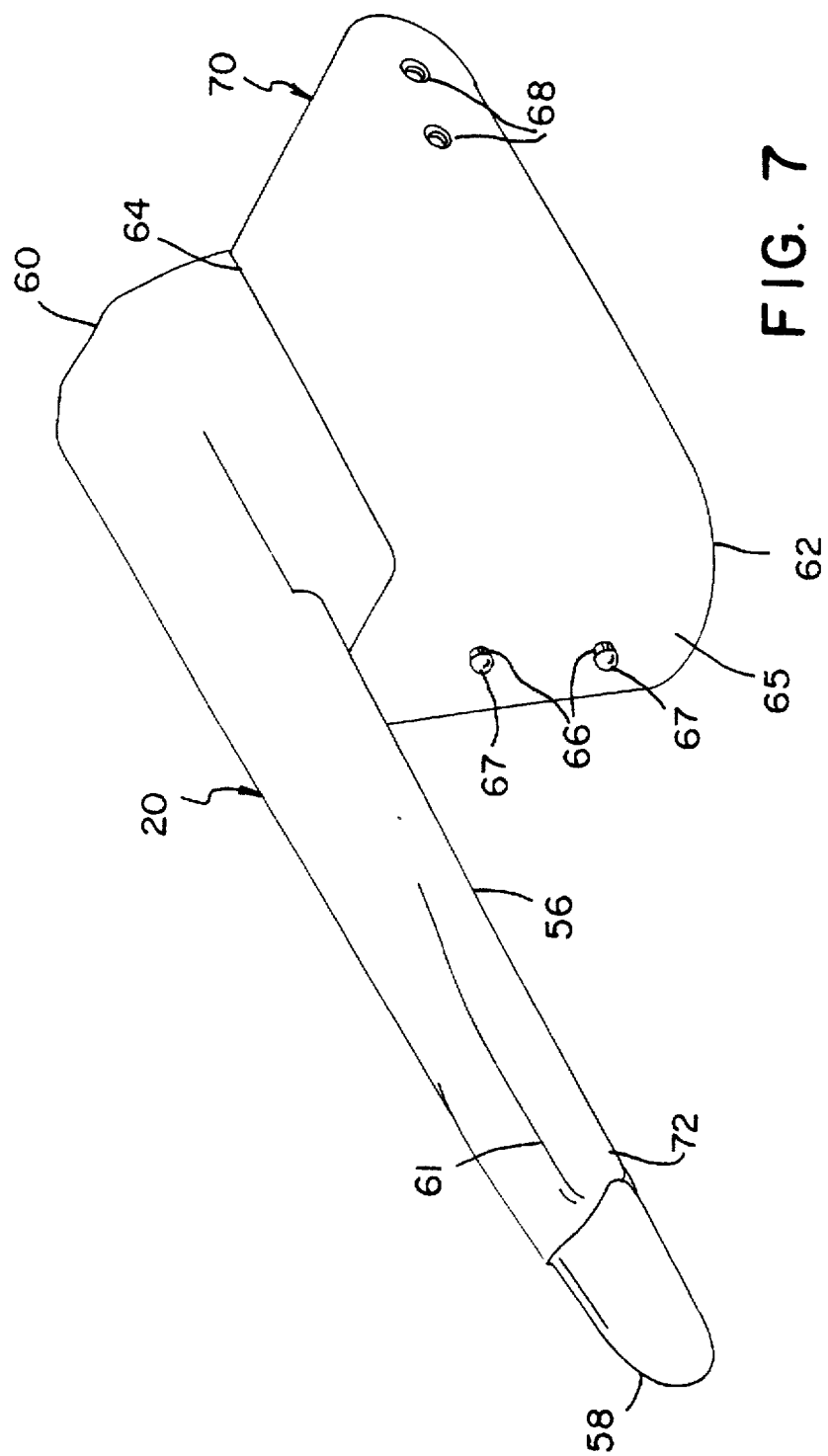

DISPOSABLE PROTECTIVE SLEEVE FOR A LARYNGOSCOPE AND METHOD OF USING THE SAME

FIELD OF THE INVENTION

The present invention relates, in general, to disposable protective covers for medical instruments, and more specifically, to a disposable protective sleeve for a laryngoscope blade and handle.

BACKGROUND OF THE INVENTION

A laryngoscope may be used by physicians or other health care professionals for inspection of patient's throats, or for manipulation of body parts. In emergency situations or during routine endotracheal intubation, health care professionals may have to use intubation procedures to establish an artificial airway. During these intubation procedures, laryngoscopes are used to keep the tongue out of the way or to visualize the epiglottis, so that an endotracheal tube can be inserted into the trachea.

A laryngoscope is a hand-held device, consisting generally of a blade movably attached to a cylindrically shaped handle. The blade has an internal channel with an optional light source to assist a physician looking into a patient's throat. The handle is used to manipulate the blade and also to contain a power source for the light, if present. The blade is usually hingedly attached to the laryngoscope handle at a contact point, and has either a C-shaped or L-shaped lateral cross-sectional surface, with inside and outside surfaces. The outside surface is shaped to conform to the interior features of the patient's throat, and to facilitate lifting the patient's tongue, upon insertion of the blade into the patient's mouth and throat. The inside surface of the blade typically curves partially inwardly to define a space, which includes a guide surface, through which the physician can sight down the patient's throat. Several different blade shapes are in general use. Three common blade styles having distinctly different shapes are (in typical nomenclature) the "Wisconsin" straight blade, the "Miller" straight blade, and the "Macintosh" curved blade. Such blades also are available in different sizes to allow the size of the blade to be best matched to the patient.

Under current medical practices, instruments such as laryngoscopes should be sterilized after each use so as to avoid cross-contamination among patients. Improper sterilization could result in contraction of serious diseases such as AIDS, hepatitis, herpes, etc.

Although the laryngoscope may be manually sterilized, such methods tend to be time-consuming and burdensome for the practitioner who typically does not have time to wait. Quick sterilization of laryngoscope blades through conventional methods such as autoclaving may not be used, since the standard laryngoscope blade often includes a delicate light assembly mounted on the blade itself.

Several disposable coverings for laryngoscopes or portions thereof have been described in the prior art. Many of these prior art disposable covers cover the blade of the laryngoscope only, risking exposure of the patient to possible contamination from the connector fittings and/or the handle of the laryngoscope due to inadequate sterilization of these portions of the laryngoscope. Previous attempts to cover the portion of the laryngoscope handle which may come into contact with the patient have also been described. However, the covers tend to be shapeless "baggy" covers which do not easily conform to the contoured shape of the laryngoscope blade. Complicated vacuum evacuation systems have been suggested to conform such universal covers to the shape of the blade. Another approach which has been suggested is a condom-like elastic latex protecting barrier which consists of a series of concentric contiguous elastic portions with increasing diameters which may be placed at the tip of the laryngoscope blade and rolled over the blade and the entire handle. Although such a cover does provide protection for both the blade and handle of the laryngoscope, it does not closely follow the inwardly curved contours of the laryngoscope blade and therefore may obstruct the physician's view into the patient's throat and decrease the ability of the inner surface of the laryngoscope blade to act as a channel for the intubation tube. Such elastic covers can fit so tightly to a laryngoscope that they are difficult to put on and remove. Furthermore, most laryngoscope handles are manufactured with a knurled surface to allow a better grip for the physician using the laryngoscope. This advantage is lost if the entire handle is enveloped by a protective cover as those shown in the prior art.

Accordingly, there is a need in the medical field for a disposable cover that may be used on the different types of commonly used laryngoscope blades with varying shapes and sizes, which conforms closely to the shape of the particular blade for which it is being used, but which also allows protection of the portion of the laryngoscope handle that may come into contact with a patient.

SUMMARY OF THE INVENTION

The disposable protective sleeve of the present invention is easily placed onto a laryngoscope and provides complete coverage of those portions of the laryngoscope blade and handle likely to come in contact with a patient. The protective sleeve comprises a preformed plastic sheath portion which covers the blade and a flexible shield which covers a portion but preferably not all of the handle. The contours of the preformed sheath may be formulated via computer aided design for particular blade styles so that the preformed sheath closely conforms to the shape and contours of the blade being used. The sheath and shield may be and preferably are integrally molded together of a low cost, flexible, fluid-impervious plastic material, such as by injection molding or, preferably, by blow molding. The protective sleeve thus formed is economically disposable after each use.

The protective sleeve of the invention in a preferred form includes a contoured, fluid-impervious preformed sheath defining a hollow cavity, having an open end and a closed end, the open end having an aperture to receive a laryngoscope blade, which completely covers the portions of the laryngoscope blade that may come into contact with the patient. The preformed sheath has a semi-rigid shape which allows it to closely conform to the shape of the particular laryngoscope blade with which it is used, preferably conforming at least partially to the inwardly curved surfaces of the blade. In a preferred form, the sheath is made of light transmitting material so that it may be used with a laryngoscope blade having a light source, and, preferably, the portion of the sheath covering the light source is lens-shaped. The fluid-impervious flexible shield, which is attached along its top edge to the sheath proximate to the open end of the sheath, generally extends downwardly from the sheath at about a right angle to the laterally extending sheath. This shield is formed to cover at least the portion of the laryngoscope handle adjoining the blade and proximate to the distal end of the sheath. Generally, the shield will cover at least the front portion of the handle that faces the blade and the patient when in use. The shield is formed to define an opening through which a laryngoscope blade can be inserted into the open end of the sheath.

The sleeve also preferably includes a means for holding the sleeve on the laryngoscope. For example, the shield may additionally include a first flap which can be wrapped around the back of the laryngoscope handle to overlap another part of the shield, where the flap is secured by a fastening means. When the fastening means is secured, the sheath completely covers the blade tip and blade length, and the shield encircles and covers the portion of the handle which is likely to come in contact with a patient, typically about the top one-half or two-thirds of the handle. Because the shield does not need to seal to the handle, the shield may be secured to the handle in a non-airtight manner. The flap and fastening means serve to securely hold the disposable sleeve on the laryngoscope, preventing the disposable sleeve from accidentally slipping off the laryngoscope. The fastening means may comprise at least one peg integrally formed with and located on the shield and at least one hole in the flap, each hole of sufficient size to firmly encircle and hold each peg, such that when the flap is wrapped around the exposed handle portion to overlap the side edge of the shield, at least one peg can be inserted into and firmly held in a hole.

As an alternative for holding the sleeve on the laryngoscope, the protective sleeve can feature a rear sheath portion integrally connected to the sheath and shield such that, when the sleeve is placed on the laryngoscope, the rear sheath portion engages and covers the end of the laryngoscope blade. By engaging the end of the blade, the rear sheath portion helps hold the sleeve in place on the laryngoscope and restrains it from being inadvertently pulled off. The shield may be formed to extend only partially around the handle, covering at least the front of the handle (the portion that faces the patient) but not necessarily the back of the handle.

The sheath portion of the present invention is preferably manufactured to be specifically contoured for a particular one of the various styles and sizes of laryngoscope blades known in the art. The molding of the plastic sheath gives it a semi-rigid shape that generally matches a selected blade size and shape. This contoured design allows the sheath to be easily slid over the appropriate blade with minimal friction and without external lubrication, facilitating easy attachment of the sleeve to and removal of the sleeve from the laryngoscope without requiring that the sheath be stretched to draw it onto the blade. The contours of the semi-rigid sheath also preferably partially parallel the inwardly curved surfaces of the blade so that a line of sight for the user is provided. Preferably, the inner dimensions of the preformed sheath are slightly greater than the dimensions of the blade to further facilitate insertion of the blade into the sheath. The sheath is also preferably made from a material sufficiently flexible such that the sheath will distort as necessary to conform to the shape of the laryngoscope blade, thus minimizing any obstruction of the operator's view of the patient's throat. The sheath is manufactured in such a manner so as to be flexible enough to fit on a curved laryngoscope blade but rigid enough to hold the lateral shape of the blade prior to installation on the laryngoscope blade. For example, the sheath for a curved laryngoscope blade may be straight in the longitudinal dimension as molded to facilitate the molding operation, but will be sufficiently flexible to bend to conform to the shape of the blade as it is drawn onto the blade.

Further objects, features and advantages of the invention will be apparent from the following detailed description when taken in conjunction with the accompanying drawings.

BRIEF DESCRIPTION OF THE DRAWINGS

In the drawings:

FIG. 7 is a left front perspective view of the protective sleeve of the present invention.

DETAILED DESCRIPTION OF THE INVENTION

Figure 1:
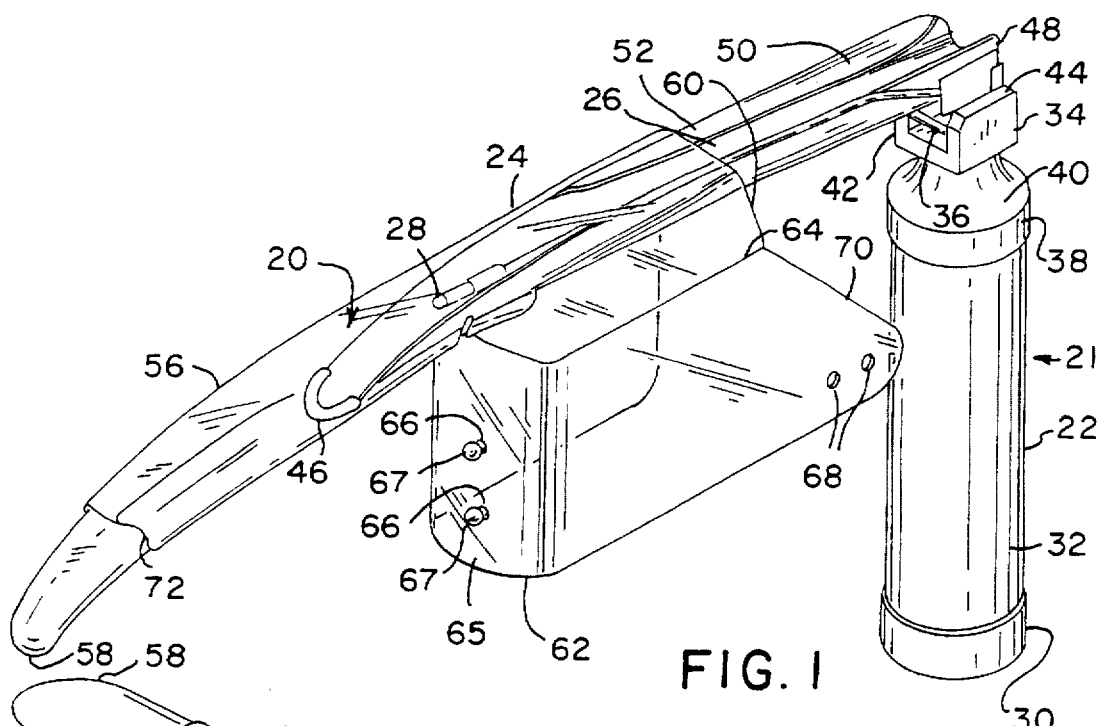
FIG. 1 is a perspective view of a protective sleeve according to the invention into which a typical laryngoscope blade of a laryngoscope is shown partially inserted.

With reference to the drawings, in which the same reference numerals are associated with the same parts throughout, a protective sleeve 20 in accordance with the invention is shown partially drawn onto a typical laryngoscope 21 used by a physician or other health care provider. To best illustrate the functions and advantages of the invention, the structure of the laryngoscope 21 will be first described below.

The typical laryngoscope 21 includes a handle 22 and a blade 24, and is used to perform endotracheal intubation. The blade 24 has an inner surface 26 which is curved laterally and acts as a guide surface which the physician can sight down to view into the patient's throat and which can be used to guide an intubation tube. A small electric lamp 28 is (typically) mounted adjacent to one edge of the blade 24 to assist in viewing the larynx and throat. It is understood that the invention may be used with any type of laryngoscope blade. For purposes of a non-limiting example only, a Miller blade is illustrated in FIG. 1 as the blade 24. A cap 30 is screwed onto the bottom end of the laryngoscope handle 22. The handle 22 houses one or more batteries, for example, two "C" batteries (not shown). The batteries are insertable into a tubular housing 32 of the handle 22 by unscrewing the cap 30 to allow access to a hollow battery chamber inside the handle 22. A U-section support 34 on the top end of the handle 22 provides a pivotal support for the blade 24 via a pivotal rod 36, as explained below. A collar 38 is rigidly attached to the housing 32 and is integrally connected to the support 36 via an integral neck 40. The pivot rod 36 spans flanges 42 and 44 of the U-section support 34. The lamp 28 is mounted at the end of an electrical supply wire (alternatively, an optical fiber can direct light from a remote position to a tip at the position of the lamp 28) which extends longitudinally between a blade tip 46 and a blade back end 48. The lamp 28 on the blade is electrically connected to the handle by the wire.

The blade 24 may be one of a variety of blades commonly available for the laryngoscope 21. The shape of the blade length 50 defines the style of blade. The most common blades are the curved Macintosh blade, the straight Jackson or Wisconsin blade, and, as illustrated in FIG. 1, the straight Miller blade with a curved portion proximate to the tip. The laryngoscopist has a choice of which blade style to use, and the choice is most often a personal preference. The blade 24 may also be of different sizes, adapted for specialty needs, for example, larger sizes for adults and smaller sizes appropriate for infants and children. The blade 24 is generally made of a material that is durable and easy to clean. Conventionally, stainless steel is used.

In the type of blade 24 shown in FIG. 1, the blade cross-section is arcuate, generally curving transversely from one edge of the blade 24 to a flange 52 that extends inwardly of the curvature. In use, the blade 24 serves to roll the tongue of a patient out of the way and allow the laryngoscopist to sight under the arc of the blade 24. The blade 24 shown in FIG. 1 also curves somewhat longitudinally, but other available blades are straight or have a combination of curved and straight sections along their length. The flange 52 is not present in some specialty blades adapted for patients with restricted mouth openings but the blades usually have an inward curvature. As shown in FIG. 1, the tip 46 of the blade 24 is rounded or blunted with a structural lip so that, when the blade 24 is slid along the oral mucosa with the tip 46 leading, there is some protection against the edge of the blade 24 scraping the oral mucosa.

Figure 2:
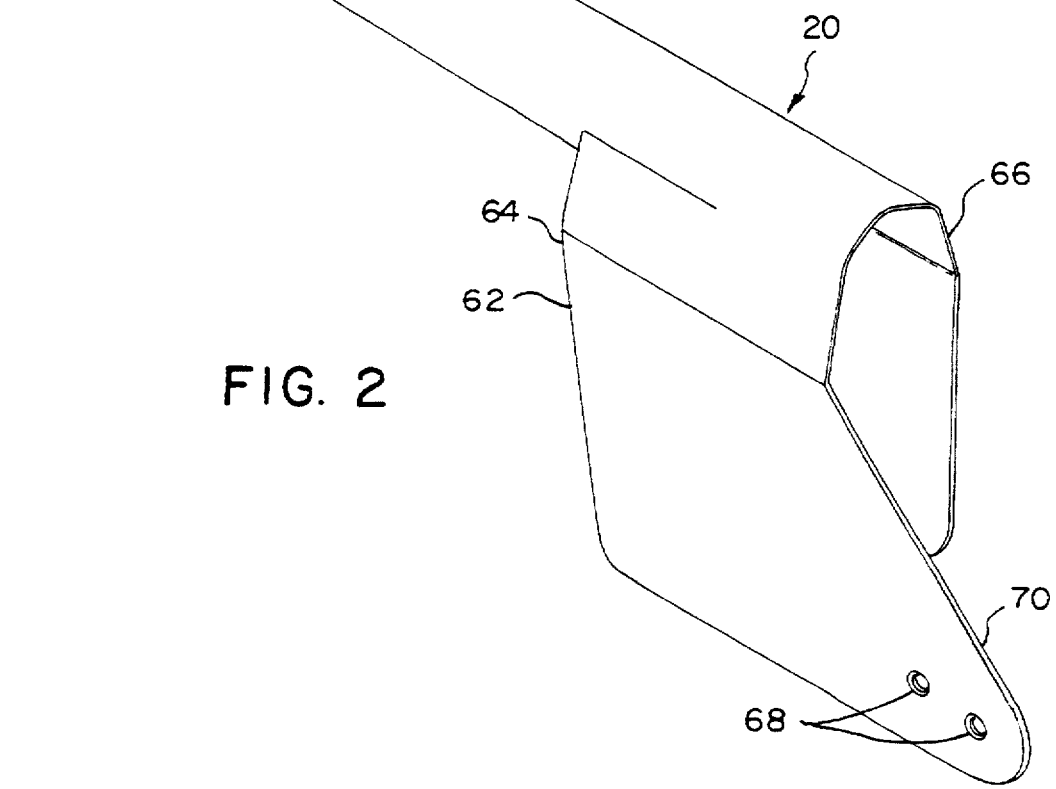
FIG. 2 is a left rear perspective view of the protective sleeve of the present invention.
Figure 3:
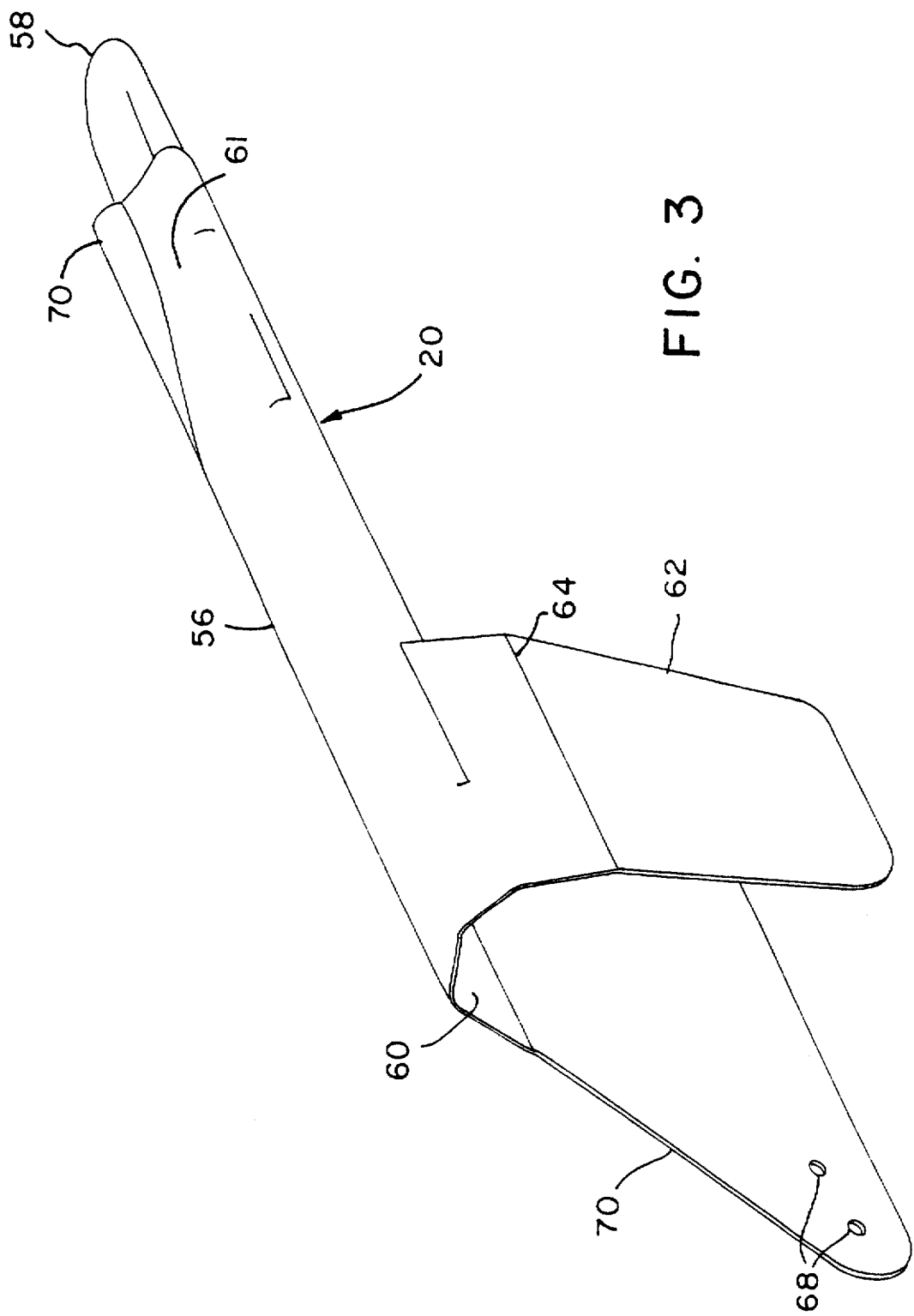
FIG. 3 is a right rear perspective view of the protective sleeve of the present invention.
Figure 4:
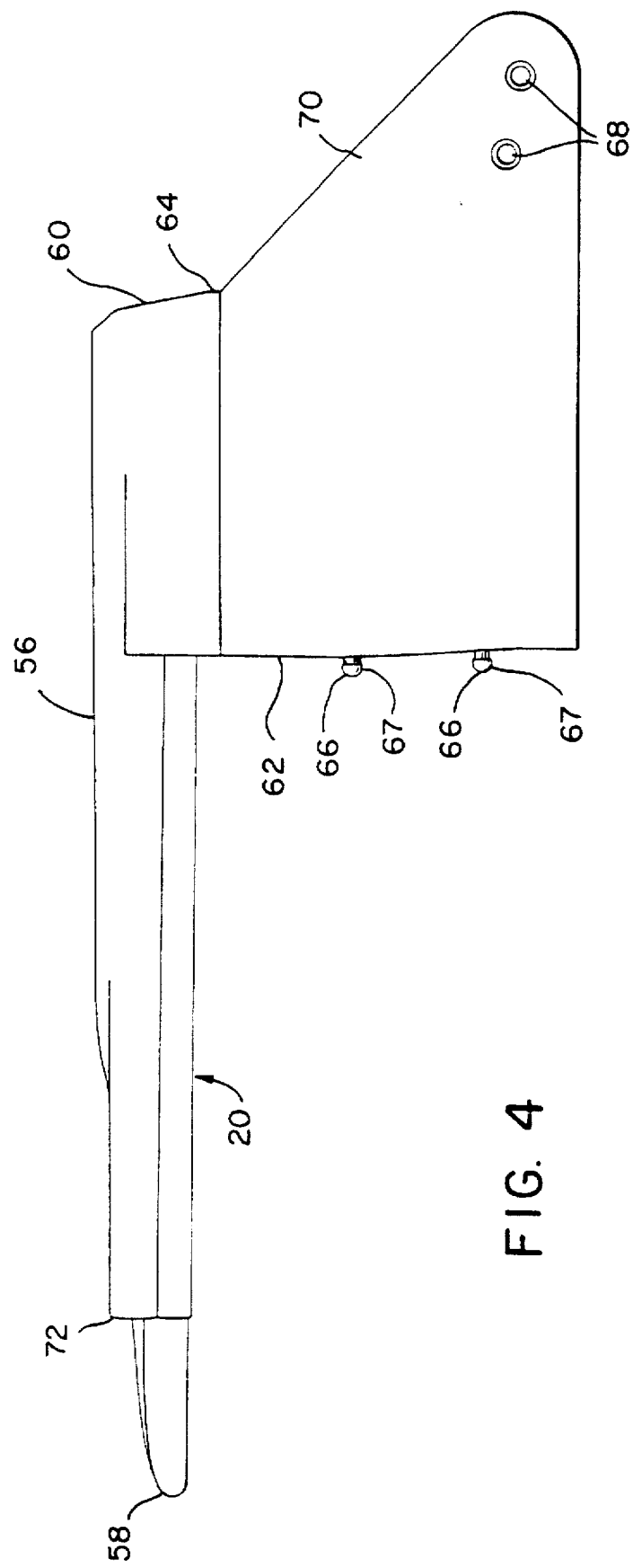
FIG. 4 is a left side view of the protective sleeve of the present invention.

The disposable protective sleeve 20 for a laryngoscope in accordance with the present invention is also shown in FIG. 1. The sleeve 20 has a preformed sheath 56 having a closed end 58 and an open end 60. The sleeve 20 also includes a shield 62 which is preferably integrally connected at its top edge 64 to the sheath at the open end 60 of the sheath 56, as shown in the views of FIGS. 2–4.

The preformed sheath 56 of the sleeve 20 is preferably molded of plastic such that the sheath 56 retains a semi-rigid shape which closely conforms to the blade 24. This form fitting shape allows the sheath to maintain close contact with the entire outside surface of the blade when it is in place. Form fitting preformed sheaths may be manufactured for each individual blade type and size, and such designs can be readily obtained using computer aided design techniques well known in the art. By molding the sheath portion of the sleeve to closely conform to the style and size of blade on which the protective sleeve is to be used, several advantages are realized. These advantages include the fact that any obstruction of the operator's view caused by the protective sleeve is minimized. For laryngoscope blades having inwardly curving surfaces, the sheath also preferably is formed to have a portion 61 which is at least partially parallel to the inwardly curving surfaces to provide a line of sight for the user, which also facilitates insertion of a tube along the laryngoscope blade. Additionally, the molded design allows the operator to easily slide the sleeve on or off the laryngoscope blade with a minimal amount of effort. In contrast, prior "condom" like protective sleeves which are elastically stretched over the blade are often difficult to properly mount on the blade, and are also sometimes difficult to remove. Further, the preformed but close fitting design helps to minimize the volume occupied by the sleeve itself so that the sleeve does not make insertion of a protected blade into the throat more difficult.

Figure 8:
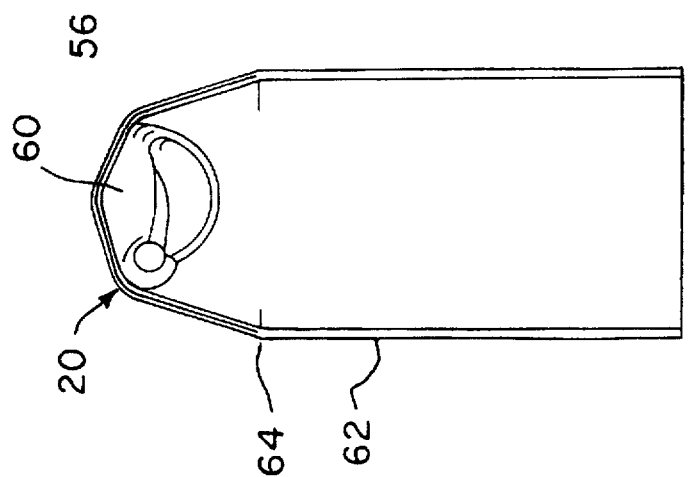
FIG. 8 is a back view of the protective sleeve of the present invention.
Figure 5:
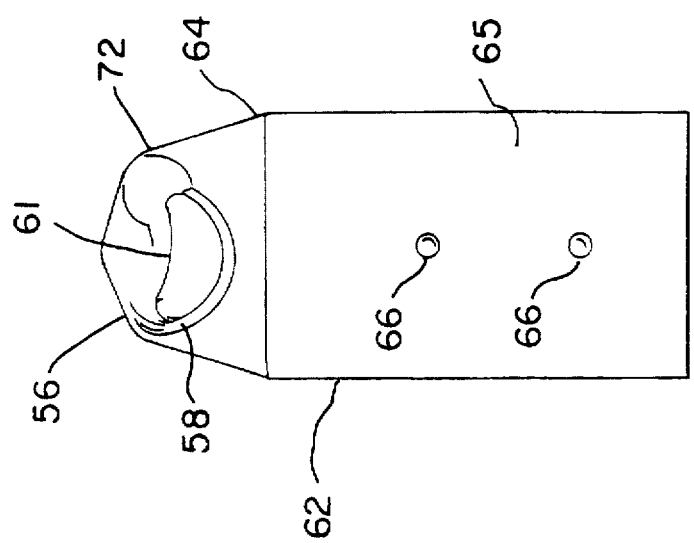
FIG. 5 is a front view of the protective sleeve of the present invention.
Figure 6:
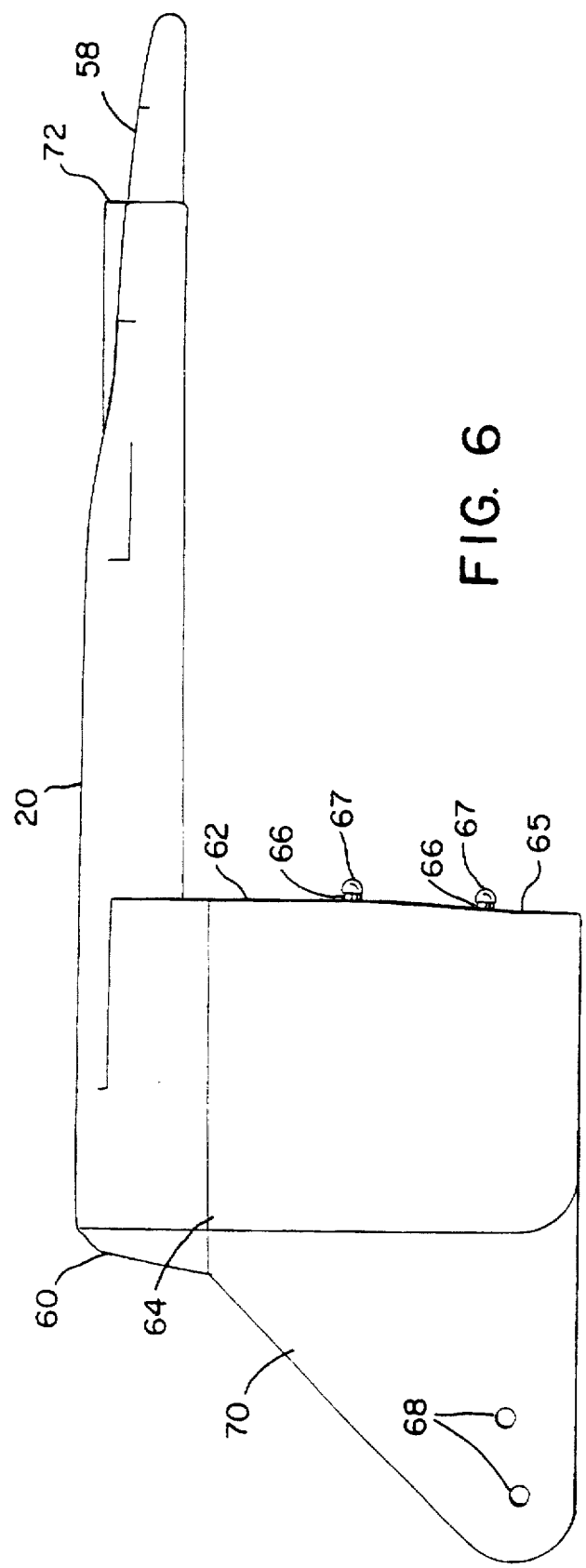
FIG. 6 is a right side view of the protective sleeve of the present invention.
Figure 9:
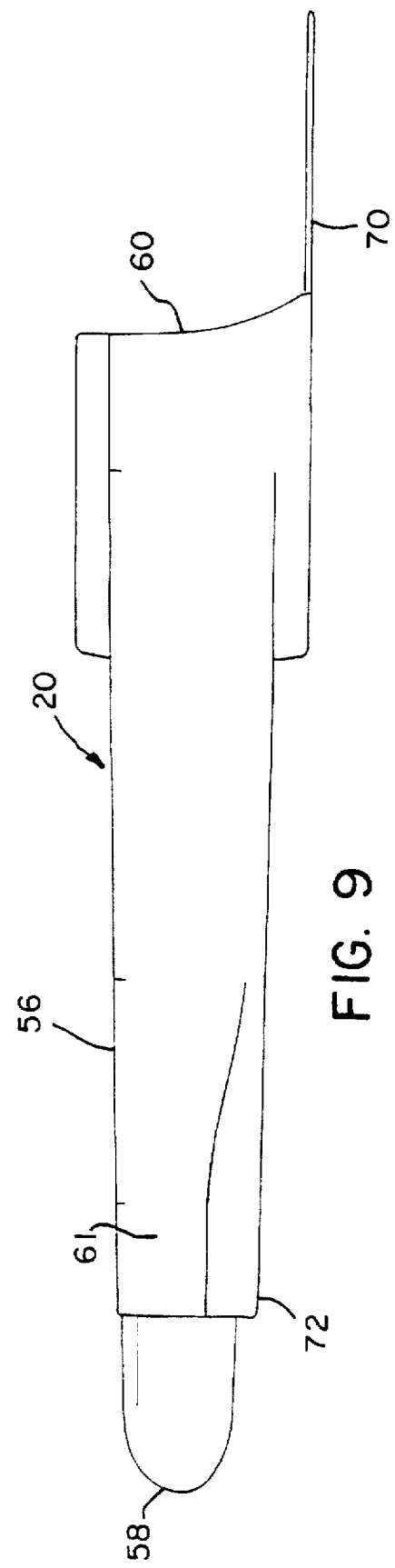
FIG. 9 is a top view of the protective sleeve of the present invention.

The shield 62 is formed to cover the portion of the laryngoscope handle 22 where it joins the blade 24 and proximate to the distal end of the sheath 56. In this manner at least the portion of the handle facing the patient is covered. The shield 62 may additionally includes a means for holding the protective sleeve on the laryngoscope to avoid unintended removal or displacement of the protective sleeve during use. The shield is integrally connected to the sheath, with both pieces preferably molded together as described below. As best illustrated in FIGS. 2, 3, and 8, the shield 62 defines an opening through which the laryngoscope blade 24 can be inserted into the open end of the sheath.

Figure 11:
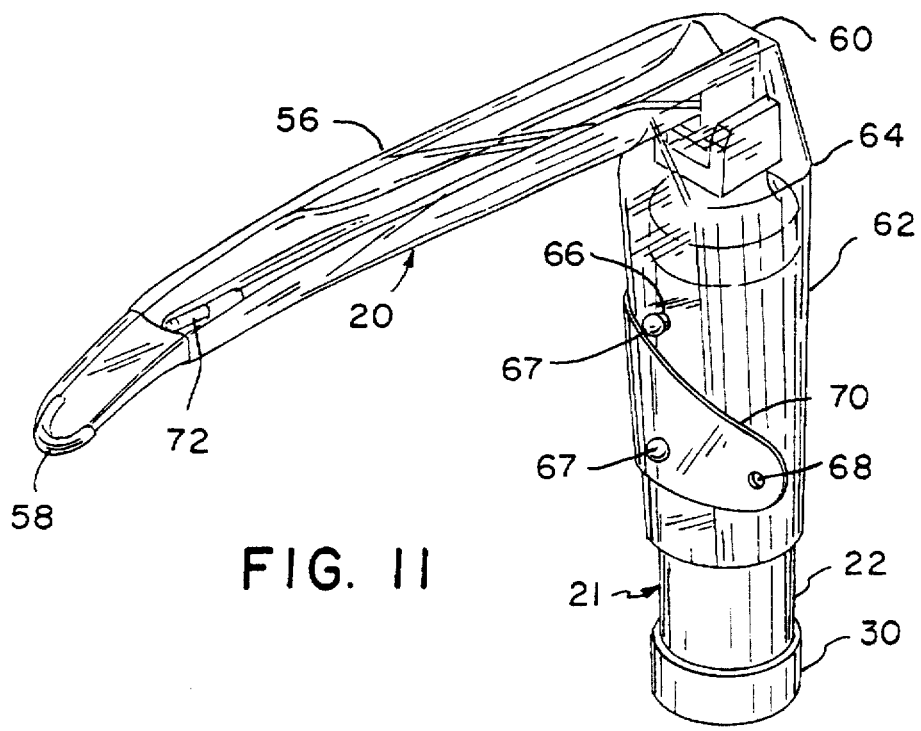
FIG. 11 illustrates a protective sleeve installed on a laryngoscope in accordance with the present invention with the blade being in an active position to turn on the lamp.
Figure 10:
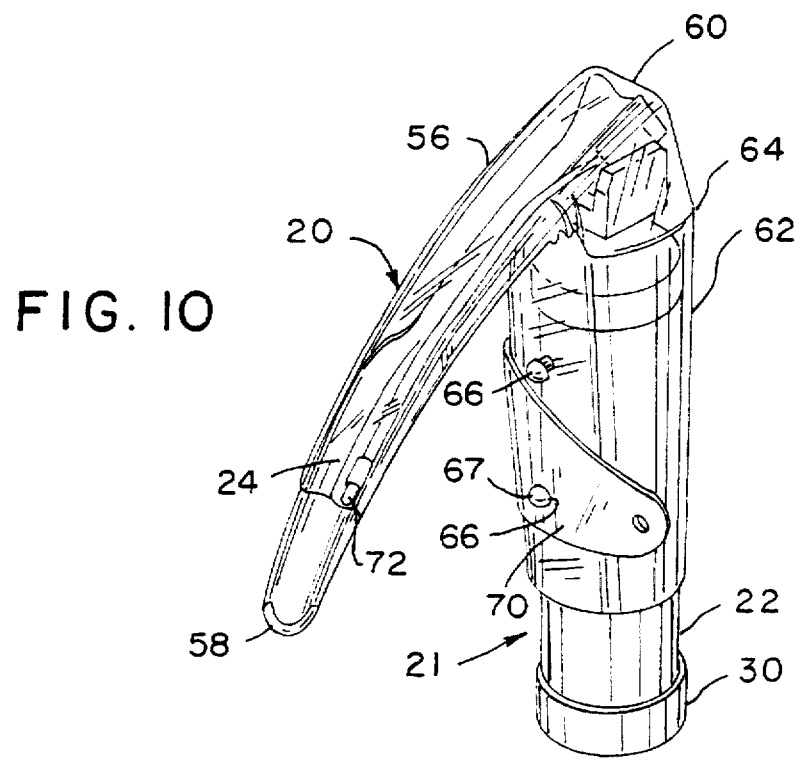
FIG. 10 illustrates a protective sleeve installed on a laryngoscope in accordance with the present invention, with the blade being in an inactive position.

An example of structure which provides means for holding the sleeve 20 on the laryngoscope 21 is shown in FIGS. 1–10. One or more pegs 66 are located on a portion 65 of the shield 62 which is proximate to the sheath 56. The pegs 66 also may be integrally molded to the shield 62 from the same material as that of which the shield is formed. The pegs 66 may have a flared tip 67 distal to the position of attachment of the pegs to the shield 62. At least one accompanying hole 68 is located on a rear flap 70 of the shield 62. The rear flap 70 can then be wrapped around the handle 22 to overlap the portion 65 of the shield, and the pegs 66 can be inserted through a hole or holes 68 to hold the shield (and the entire sleeve) in place, as shown in FIGS. 10 and 11. By providing more than one hole 68 and more than one peg 66, the user can fasten the shield in place relatively tightly to handles 22 of various sizes. Alternate fasteners for the shield flap 70 may also be used, and may consist of any suitable fastening means known in the art. Such means may consist of known fasteners such as Velcro®, zippers, chemical or adhesive sealants, and a linear or circular elastic band, wire, plastic, rubber or other similar material which may be wrapped around or twisted around the shield portion to hold the sleeve in place, and any other fastening means providing appropriate holding characteristics. The mechanisms described herein preferably allow easy fastening of the sleeve to and removal of the sleeve 20 from the laryngoscope blade 24 and handle 22.

The open design of the shield 62 allows the protective sleeve 20 to accommodate various lengths and diameters of laryngoscope handles. The sheath 56 is attached to the shield 62 in such a manner so as to allow the back of both the shield and the sheath to be open. Further, the bottom of the shield 62 is open so that the protective sleeve 54 may be easily installed on the laryngoscope 20.

The protective sleeve is preferably made of a relatively flexible, somewhat elastic but semi-rigid, and fluid impervious synthetic polymer plastic, for example, low density polyethylene (LDPE) or ethylene vinyl acetate (EVA), or mixtures thereof, that may be constructed such that the molded sheath fits closely to a particular style of blade and generally retains a shape which conforms to the shape of the blade prior to being placed on the blade. The sheath and shield may be formed integrally by injection molding or blow molding, or by other processes as desired, such as thermoforming, stretch forming, or by a solution process such as coating or dipping.

The material of the sleeve may be sterilizable, and the sterilized sleeve can be held in packaging where is kept in sterile condition until it is used if desired, although sterilization of the sleeve is not generally necessary since it typically will not be in contact with open wounds. The sheath is preferably manufactured to dimensions slightly wider than the width of a particular laryngoscope blade to allow easy installation and removal from the blade. The flexible, somewhat elastic plastic material from which the protective sleeve is constructed will also act as a cushion to help protect the teeth of the patient as the laryngoscope is inserted and removed and if the laryngoscope is used unconsciously by the laryngoscopist as a lever when manipulating the blade to expose the patient's larynx. The material of the sheath may be selected in thickness in the general range from 0.001 inch to 0.120 inch. Preferably, the sheath material has a thickness of approximately 0.040 inch, and the shield portion has a thickness of approximately 0.060 inch, for materials such as LDPE or EVA.

The preformed sheath 56 need not necessarily precisely form-fit to the blade, as the material of the sleeve is preferably somewhat flexible such that, as the sheath is drawn over the blade the material of the sheath will bend and flex to conform more closely to the actual longitudinal curvature of the laryngoscope blade. However, unlike prior elastomeric protectors, the material of the sleeve is also preferably rigid enough to retain generally the lateral shape of the blade prior to the installation of the sleeve on the blade for the benefits discussed above.

The plastic of the sheath is preferably also substantially transparent or translucent to allow transmission of light from the lamp 28 of the laryngoscope 21. In a preferred design, the portion 72 of the sheath 56 which covers the lamp 28 will be somewhat lens-shaped to focus and concentrate the light.

Figure 12:
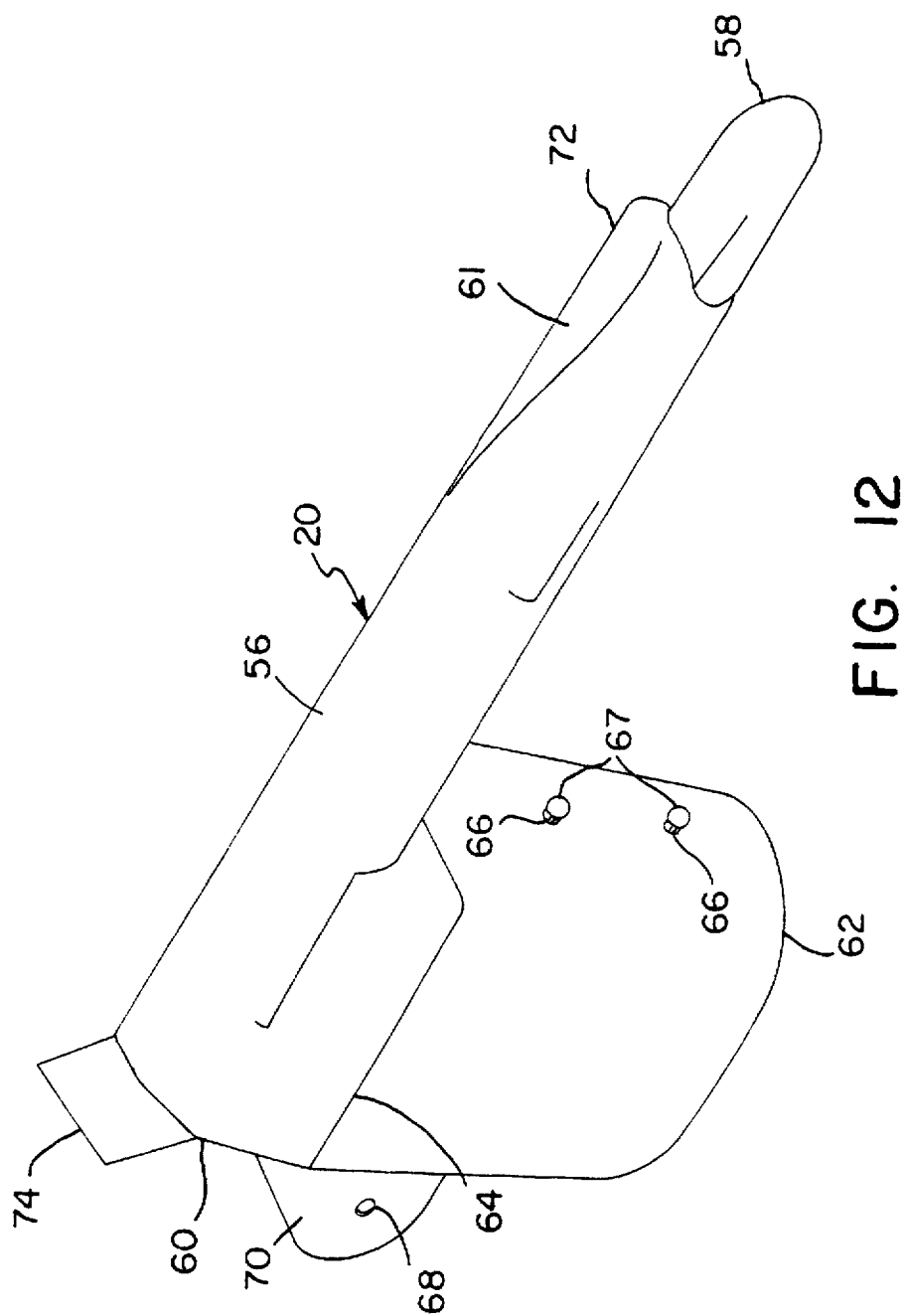
FIG. 12 is a right front perspective view of an alternative embodiment of a protective sleeve according to the present invention.

When the sleeve 20 is to be used by a health care professional, the tip 46 of the laryngoscope blade 24 is inserted into the open end 60 of the sleeve, and the sheath 56 is then drawn over the blade 24, as illustrated in FIG. 1. The handle 22 of the laryngoscope may be attached to the blade 24 before or after the blade 24 is inserted into the sheath 56. As noted above, the dimensions of the sheath are preferably somewhat larger than the blade, and the material forming the sheath preferably has a relatively low friction inner surface such that the sheath 56 may easily be drawn over the blade 24. As shown in the embodiment of FIG. 12, the sheath 56 may optionally have attached thereto a pull tab 74, which can be grasped by the user to assist in drawing the sheath 56 over the blade 24.

After the protective sleeve 54 is placed over the blade 24, and the handle 22 of the laryngoscope 20 is attached, the laryngoscope may be moved from the inactive position of the blade 24, shown in FIG. 10, to the active position of the blade, shown in FIG. 11. The back end 48 of the blade 24, distal to the blade tip 46, typically has attached thereto a pivot arm which extends perpendicularly from the upper surface of the blade 24. The arm has a slot which effects a hook configuration so that the arm hooks around the pivot rod 36 of the handle 22 (as shown in FIG. 1). The U-section 34 typically has releasable stops to stop the pivot arm in at least two positions and thus present the blade 24 in at least two positions. One position in which blade 24 is presented is the "on" position wherein the lamp 28 is activated, with the blade generally perpendicular to the handle 22 as shown in FIG. 11; the other is the "off" position wherein the lamp 28 is inactivated and the blade is at an acute angle less than the perpendicular position, as shown in FIG. 10. The folded position is for non-use and for unhooking the blade 24 from the handle 22. The generally perpendicular position is the position at which the laryngoscope 21 is used. When in the perpendicular position, electrical power is provided to the lamp 28 from the batteries in the handle 22 through a switch or contact (not shown) in the handle which is closed when the laryngoscope is in this position.

An advantage of the present invention is that the semirigid integral connection of the sheath 56 to the shield 62 maintains a semi-rigid relation between the sheath and shield so that the sleeve will restrain the blade from rotating down in the off-position and contacting the handle. FIG. 10 illustrates the typical maximum downward rotation of the blade. Consequently, the chance of spreading infection as a result of accidental contact of the sheath 56 to the unprotected handle 22 is minimized.

After the blade 24 is inserted into the sheath 56 and the handle 22 of the laryngoscope is attached to the blade 24, the rear flap 70 is wrapped around the exposed portion of the handle 22 such that at least one of the holes 68 lines up with at least one of the pegs 66, as shown in FIGS. 10 and 11. At least one of the pegs 66 is secured through the hole(s) 68, and the disposable sleeve 54 is thereby firmly secured to the laryngoscope 21.

Figure 13:
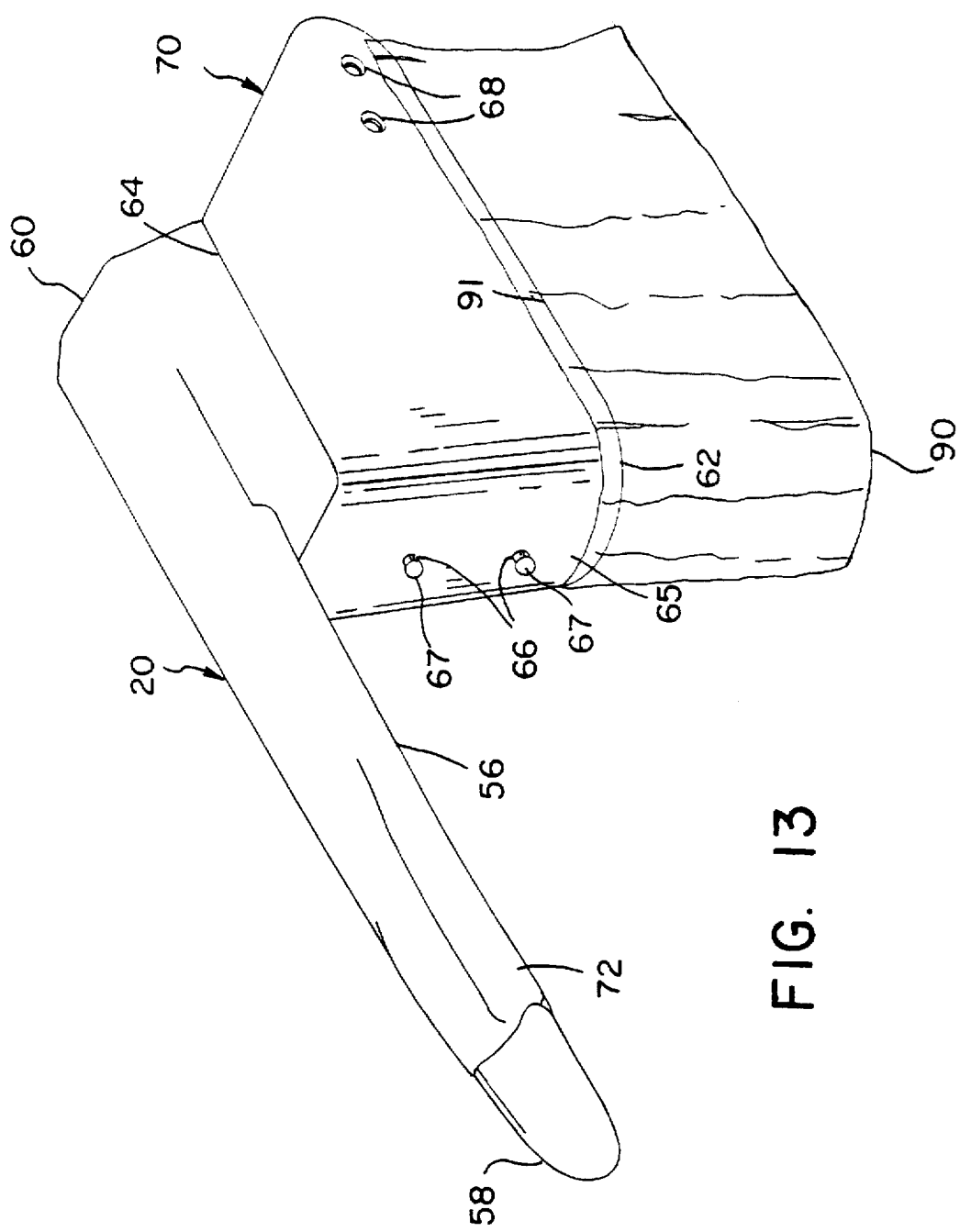
FIG. 13 is a left front perspective view of a modified embodiment of the protective sleeve which includes a flexible skirt attached to the shield to allow the entire handle of a laryngoscope to be covered.
Figure 14:
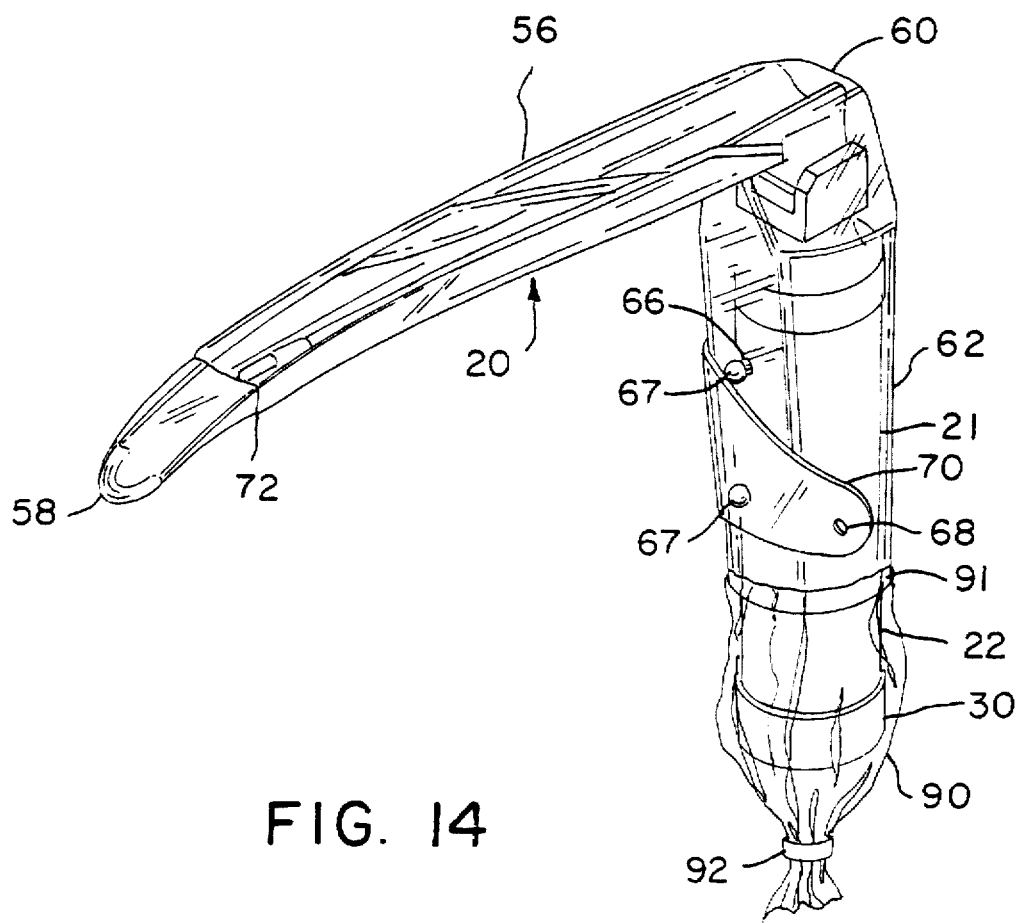
FIG. 14 is a perspective view showing the protective sleeve of FIG. 13 in place on a laryngoscope.
Figure 15:
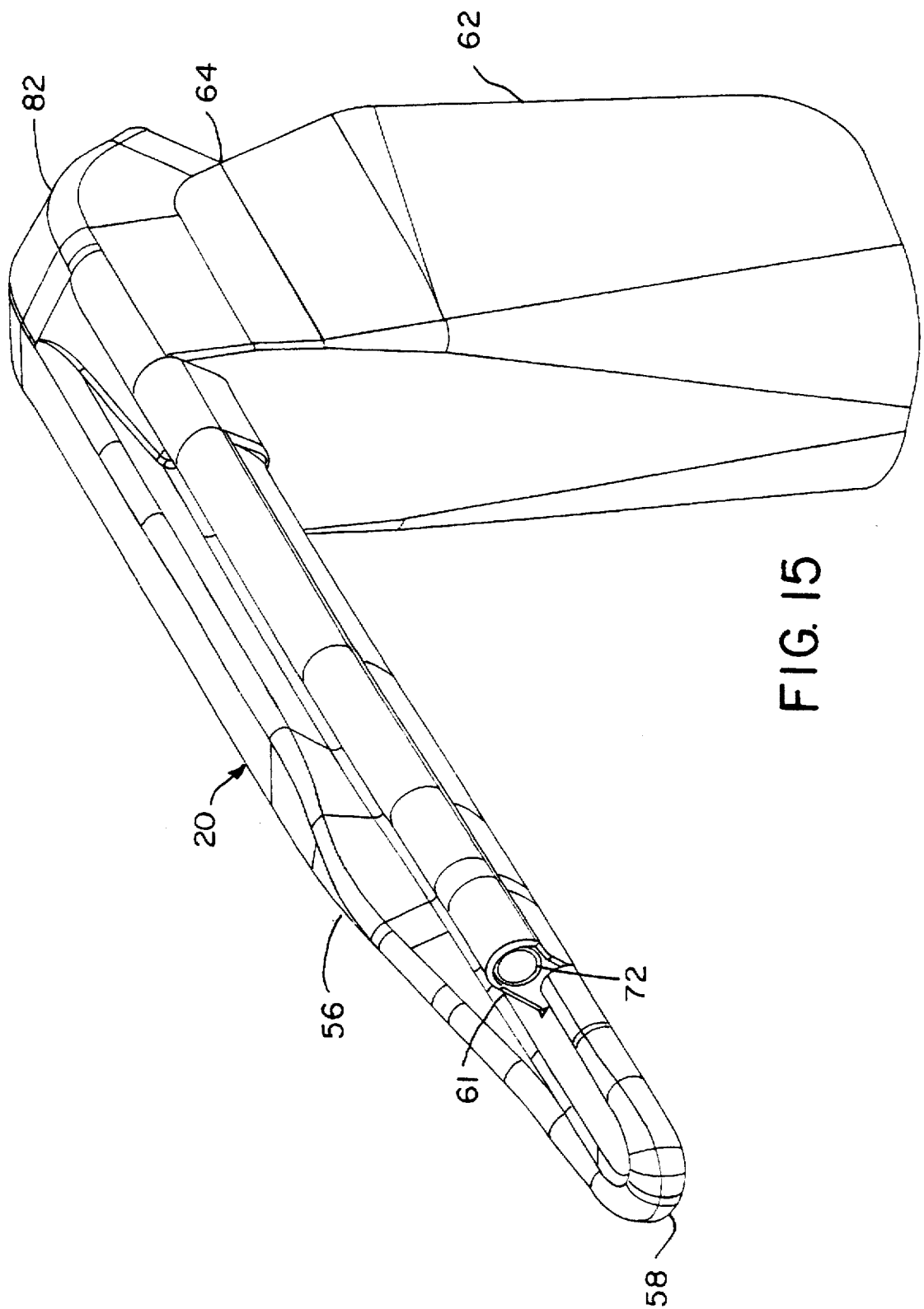
FIG. 15 is a left front perspective view of an alternative embodiment of a protective sleeve of the present invention.
Figure 16:
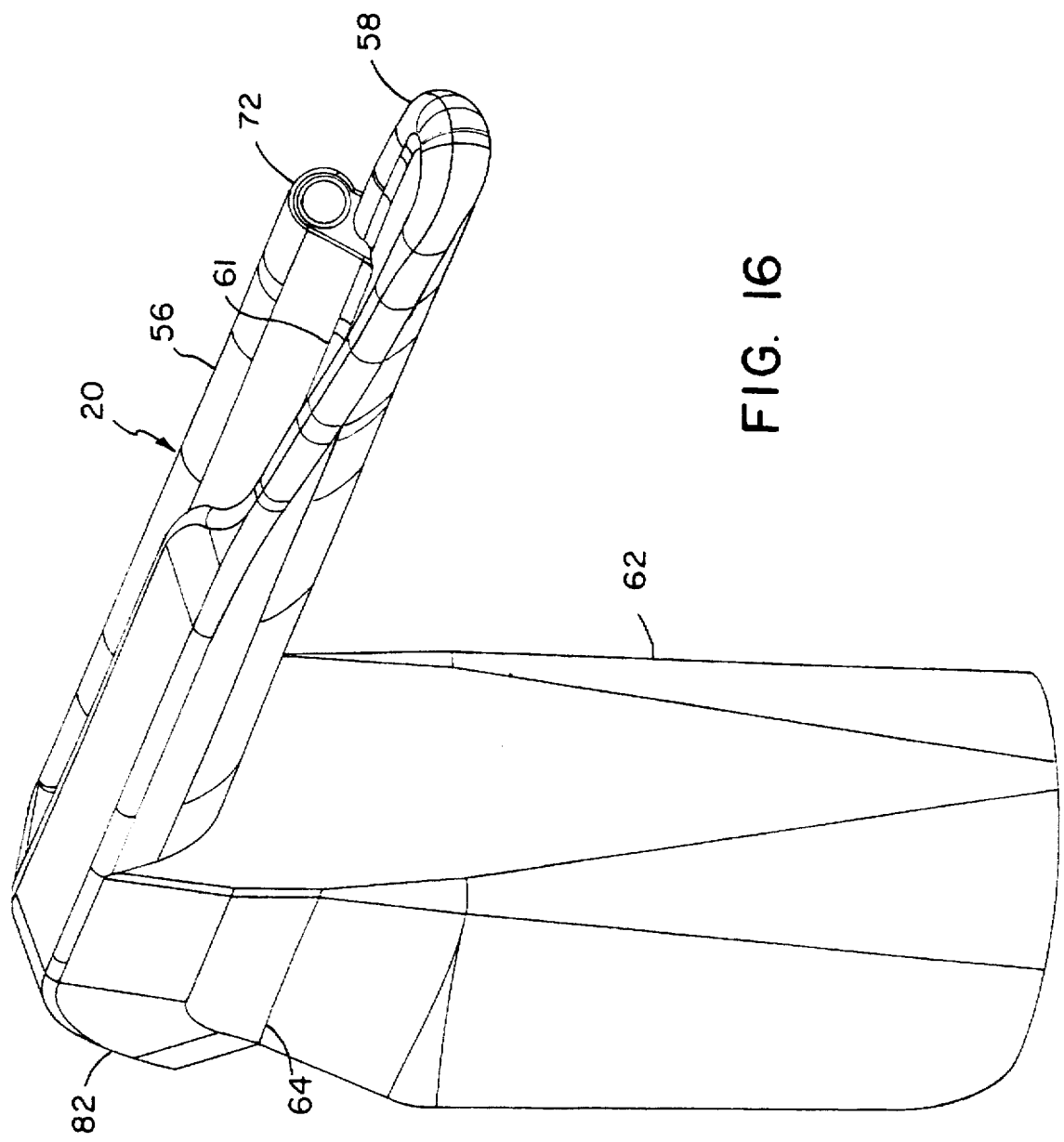
FIG. 16 is a right front perspective view of the protective sleeve of FIG. 15.
Figure 17:
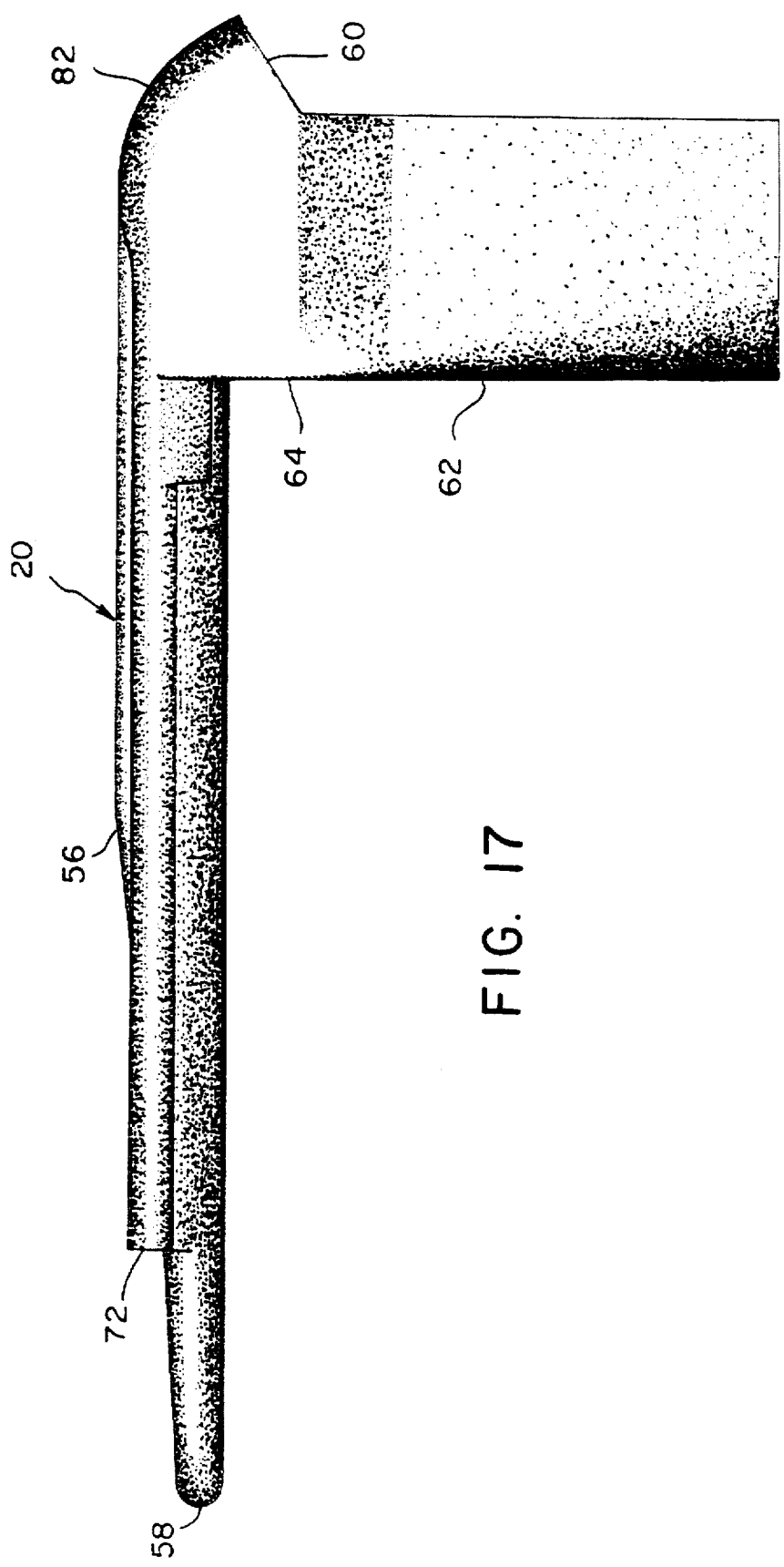
FIG. 17 is a side view of the protective sleeve of FIG. 15.
Figure 18:
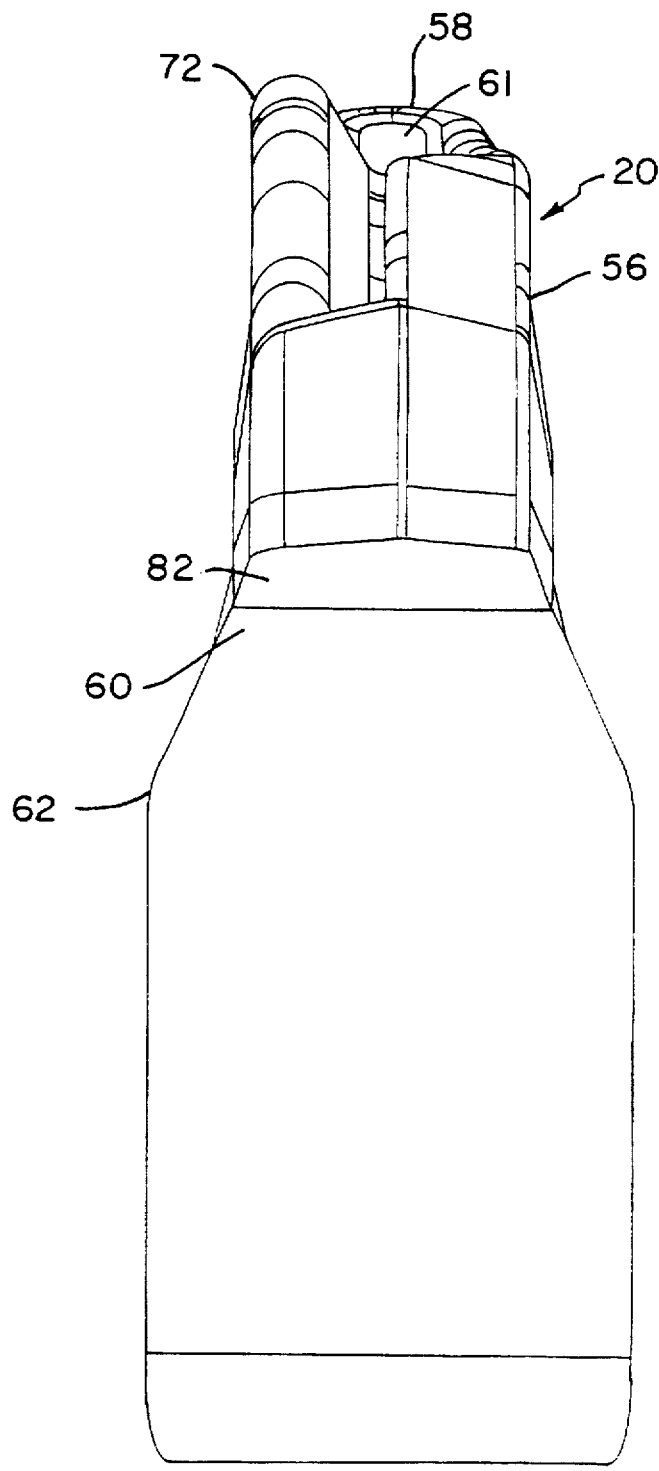
FIG. 18 is a back view of the protective sleeve of FIG. 15.
Figure 19:
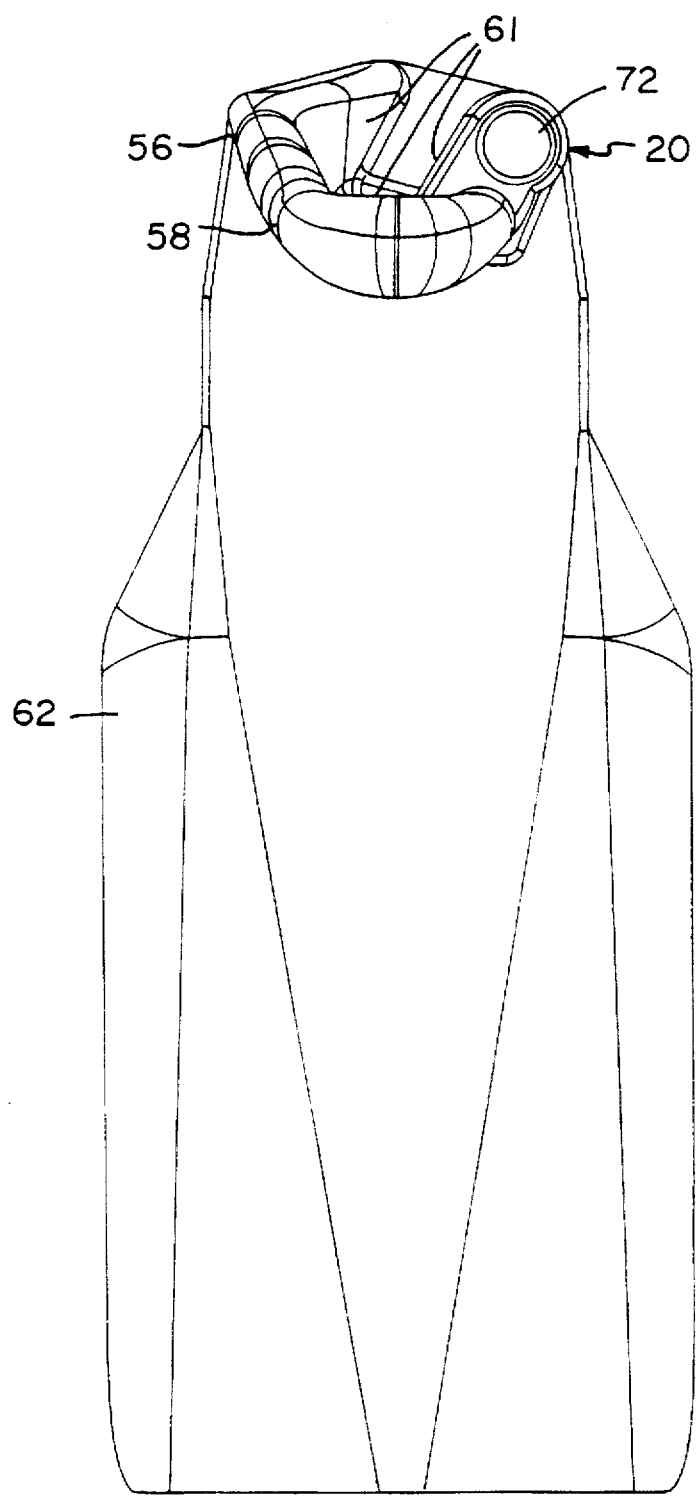
FIG. 19 is a front view of the protective sleeve of FIG. 15.

The laryngoscope 21 may be left uncovered at the lower surface of the handle 22, as this part of the laryngoscope is unlikely to come in contact with the patient, or to the sheath for the reasons noted above. Since the operator wears gloves during the intubation process, it is deemed desirable to maintain a firm grip of the handle 22 during this procedure. Most laryngoscope handles are manufactured with a knurled surface to allow a better grip for the operator; this advantage is lost if the entire handle is covered. Some operators may find they have less "feel" and control of the handle if there are two layers, i.e., the operator's glove and the disposable sleeve, between the operator's hand and the handle 22, and may thus object to a sleeve which covers the entire handle. However, other laryngoscope users may prefer that the entire handle 22 be protected. This may be accomplished by extending the length of shield 62 to the full length of the handle 22, or by adding an additional flexible handle cover 90 as shown in FIGS. 13 and 14, which is attached to the bottom of the shield at a strip 91 by adhesive heat welding, etc. The material of the skirt cover 90 may be a very flexible and pliable plastic which can be gathered under the handle and secured by a clasp 92 as shown in FIG. 14 to completely enclose the handle. A handle cover may alternatively be formed as a condom-like elastomeric cover which may be conveniently supplied in compact form where it is rolled upon itself and packaged into sterile packaging. It may then be readily installed upon a laryngoscope handle, by fitting it upon the cap 30 of the handle 22 and unrolling it over the exposed portions of handle 22. The additional cover may also comprise a suitable material formed in the shape of a sack into which the cap 30 of the handle 22 may be placed, with the sack then drawn up the handle until it overlaps the shield 62. The sack may then be secured to the shield 62 using any suitable fasteners, such as rubber bands, zippers, wires, etc.

FIGS. 15-19 illustrate an alternative embodiment of a protective sleeve 20 in accordance with the present invention which is particularly well suited to being formed by blow molding. In this embodiment, the protective sleeve 20 also comprises a sheath 56 and shield 62, with the addition of a rear sheath portion 82 that covers the blade end 48 when mounted on the laryngoscope 21. As shown in FIGS. 16-19, the rear sheath portion 82 is an integral part of the sheath 56. The rear sheath portion 82 overlaps and engages the blade end 48, thus restraining the protective sleeve 20 from slipping off the laryngoscope 21 during use and providing a means for holding the sleeve on the laryngoscope. Otherwise, the rear of the shield 62 is left open, and no flap is used to secure the shield to the handle. This construction for the sleeve readily allows the sleeve to be formed by an economical blow molding process.

It is understood that the invention is not confined to the particular embodiments set forth herein as illustrative, but embraces such modified forms thereof as come within the scope of the following claims.

What is claimed is:

1. A disposable protective sleeve for covering a laryngoscope, comprising:

a fluid-impervious preformed sheath defining a hollow cavity to enclose therein portions of a laryngoscope blade of the type having a blade tip and a blade back end connected by a continuous blade length, the sheath having an open end and a closed end, the open end having an aperture through which the blade tip may be inserted into the cavity, the sheath constructed to completely envelop the blade tip and the length of the blade and formed of a flexible plastic material molded to a preformed shape which conforms to the shape and contours of the blade tip and blade length after placement of the sheath on the blade while maintaining sufficient rigidity to retain the lateral shape of the blade prior to installation of the sheath on the blade;

a fluid-impervious flexible shield having a top edge, the top edge at least partially integrally attached to the sheath proximate to the open end of the sheath, the shield defining an opening through which a laryngoscope blade can be inserted into the open end of the sheath, the shield extending downwardly from the sheath to at least partially cover a handle of a laryngoscope when the laryngoscope blade is fully inserted into the sheath;

a means for holding the sleeve on a laryngoscope, wherein the means comprises a flap on the shield and a fastening means for securing the flap to a portion of the shield overlapped by the flap on the shield, such that when the sleeve is placed on a laryngoscope and the fastening means secured, the sheath completely covers the blade tip and blade length and the shield encircles and covers a portion of the handle, wherein the shield has a side edge and the flap is wrapped around an exposed portion of the handle after the sleeve is placed on a laryngoscope such that the flap overlaps the side edge of the shield, and the fastening means further comprising at least one peg located on the shield and the flap having at least one hole, each hole of sufficient size to firmly encircle and hold each peg, such that when the flap is wrapped around the exposed handle portion to overlap the side edge, at least one peg is engaged and firmly held in a hole, such that the sleeve is firmly attached to the laryngoscope.

2. The sleeve of claim 1 wherein the sheath is made of light transmitting material.

3. The sleeve of claim 2 wherein the sheath is adapted to cover a laryngoscope blade having a light source and the portion of the sheath covering the light source is lens shaped.

4. The sleeve of claim 1 wherein the sheath and shield are integrally molded of a material selected from the group consisting of low density polyethylene and ethylene vinyl acetate.

5. The sleeve of claim 1 further comprising a flexible plastic cover securable to the shield to cover the entire handle of a laryngoscope.

6. The sleeve of claim 1 wherein the contour of the preformed shape of the sheath has inwardly curved surfaces to at least partially conform to inwardly curved surfaces of the blade to provide a line of sight for a user.

7. A disposable protective sleeve for covering a laryngoscope, comprising:

a fluid-impervious preformed sheath defining a hollow cavity to enclose therein portions of a laryngoscope blade of the type having a blade tip and a blade back end connected by a continuous blade length, the sheath having an open end and a closed end, the open end having an aperture through which the blade tip may be inserted into the cavity, the sheath constructed to completely envelop the blade tip and the length of the blade and formed of a flexible plastic material molded to a preformed shape which conforms to the shape and contours of the blade tip and blade length after placement of the sheath on the blade while maintaining sufficient rigidity to retain the lateral shape of the blade prior to installation of the sheath on the blade; and a fluid-impervious flexible shield having a top edge, the top edge at least partially integrally attached to the sheath proximate to the open end of the sheath, the shield defining an opening through which a laryngoscope blade can be inserted into the open end of the sheath, the shield extending downwardly from the sheath to at least partially cover a handle of a laryngoscope when the laryngoscope blade is fully inserted into the sheath, wherein the sheath and shield are integrally attached to each other to maintain a semi-rigid relation between the sheath and shield so that when the sleeve is mounted on a laryngoscope, the sleeve will restrain the blade of the laryngoscope from rotating down to contact the handle of the laryngoscope.

8. The sleeve of claim 7 further including means for holding the sleeve on a laryngoscope.

9. The sleeve of claim 8 wherein the means for holding the sleeve on a laryngoscope comprises a flap on the shield and a fastening means for securing the flap to a portion of the shield overlapped by the flap on the shield, such that when the sleeve is placed on a laryngoscope and the fastening means secured, the sheath completely covers the blade tip and blade length and the shield encircles and covers a portion of the handle.

10. The sleeve of claim 9 wherein the shield has a side edge and the flap is wrapped around an exposed portion of the handle after the sleeve is placed on a laryngoscope such that the flap overlaps the side edge of the shield, and the fastening means further comprising at least one peg located on the shield and the flap having at least one hole, each hole of sufficient size to firmly encircle and hold each peg, such that when the flap is wrapped around the exposed handle portion to overlap the side edge, at least one peg is engaged and firmly held in a hole, such that the sleeve is firmly attached to the laryngoscope.

11. The sleeve of claim 8 wherein the means for holding the sleeve on a laryngoscope comprises a rear sheath portion integrally connected to the sheath and shield, such that when the sleeve is placed on a laryngoscope, the rear sheath portion engages and covers the blade back end to hold the sleeve on the laryngoscope.

12. The sleeve of claim 7 wherein the sheath is made of light transmitting material.

13. The sleeve of claim 12 wherein the sheath is adapted to cover a laryngoscope blade having a light source and the portion of the sheath covering the light source is lens shaped.

14. The sleeve of claim 7 wherein the sheath and shield are integrally molded of a material selected from the group consisting of low density polyethylene and ethylene vinyl acetate.

* * * * *